United States Patent [19]
Pangburn

[11] Patent Number: 4,572,222
[45] Date of Patent: * Feb. 25, 1986

[54] USE OF FLEXIBLE ABRASIVE PAD FOR WET ETCHING OF FINGERNAILS

[75] Inventor: William E. Pangburn, Ventura, Calif.

[73] Assignee: William W. Haefliger, Pasadena, Calif. ; a part interest

[ * ] Notice: The portion of the term of this patent subsequent to Jul. 17, 2001 has been disclaimed.

[21] Appl. No.: 407,738

[22] Filed: Aug. 13, 1982

Related U.S. Application Data

[63] Continuation-in-part of Ser. No. 356,830, Mar. 10, 1982, Pat. No. 4,459,987.

[51] Int. Cl.⁴ .............................................. A45D 29/20
[52] U.S. Cl. .................................................... 132/76.4
[58] Field of Search .............................. 132/76.4, 73; 424/70-72; 51/401

[56] References Cited

U.S. PATENT DOCUMENTS

| | | |
|---|---|---|
| 893,004 | 7/1908 | Miller . |
| 894,161 | 7/1908 | Miller . |
| 1,910,647 | 5/1933 | Steeg et al. . |
| 2,091,807 | 8/1937 | Crum .................... 51/205 |
| 2,311,060 | 2/1943 | Lurrain ................. 51/186 |
| 2,735,434 | 2/1956 | De Rossett ......... 132/76.4 |
| 3,596,661 | 8/1971 | Metz ..................... 128/355 |
| 3,910,284 | 10/1975 | Orentreich ........... 128/355 |
| 4,034,769 | 7/1977 | Nishimura ........... 132/76.4 |
| 4,055,897 | 11/1977 | Brix ................... 51/401 X |
| 4,184,499 | 1/1980 | Seidler ............... 132/75.6 |

OTHER PUBLICATIONS

Pangburn U.S. Patent Application Ser. No. 356,830.

*Primary Examiner*—Stephen C. Pellegrino
*Attorney, Agent, or Firm*—William W. Haefliger

[57] ABSTRACT

The method of wet etching a natural or artificial fingernail, that includes:
(a) providing a tough, flexible sheet of silicone polymer, the sheet carrying abrasive particulate protruding from at least one side of the sheet, and
(b) rubbing a side of the wet sheet against the surface of the wet fingernail.

4 Claims, 20 Drawing Figures

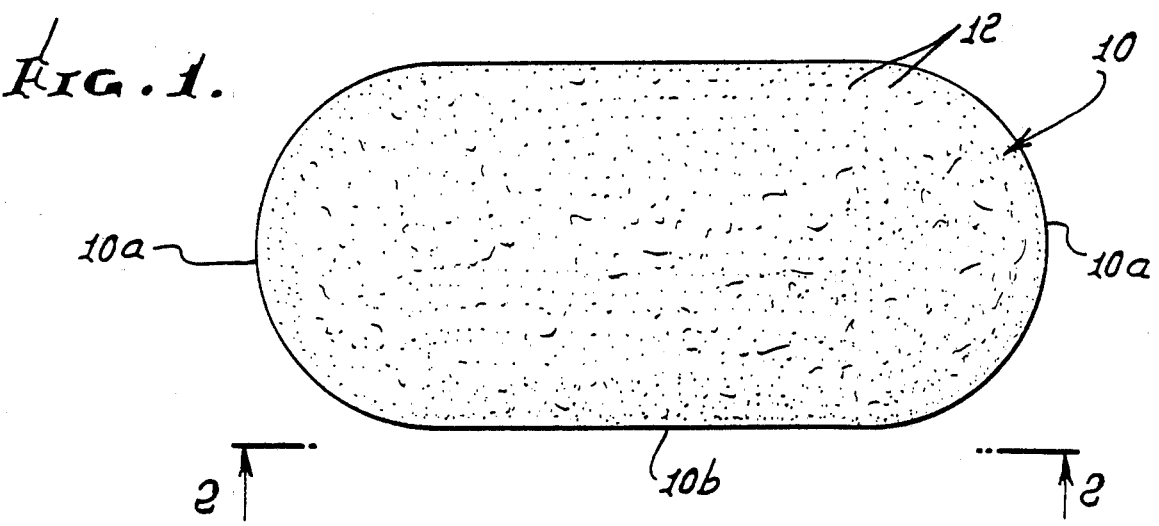
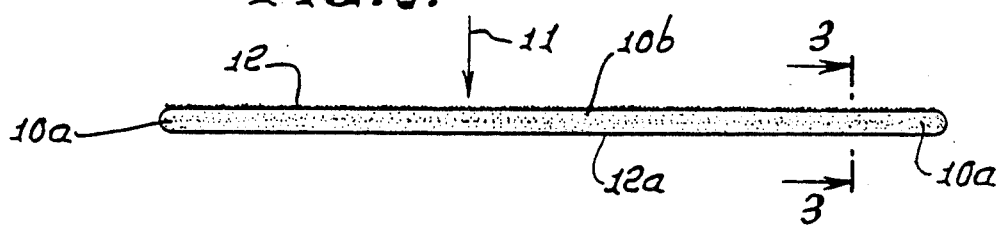
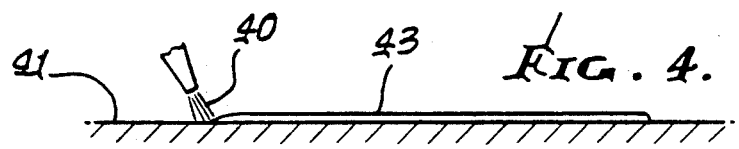
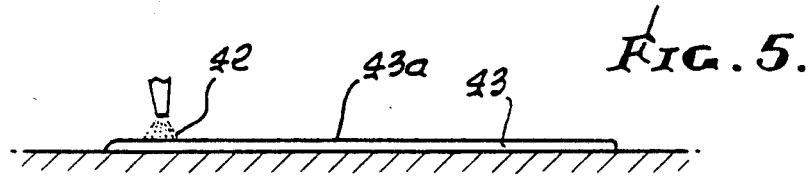
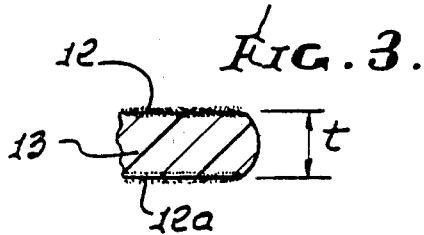
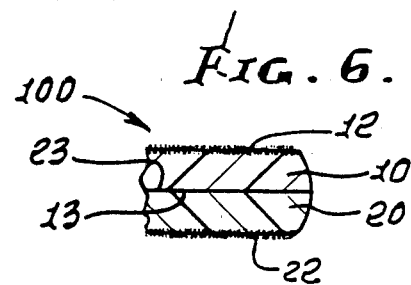
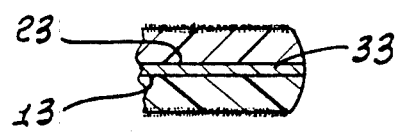
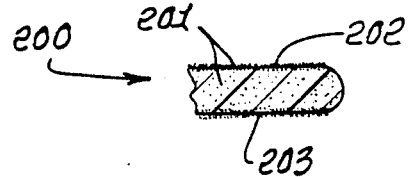

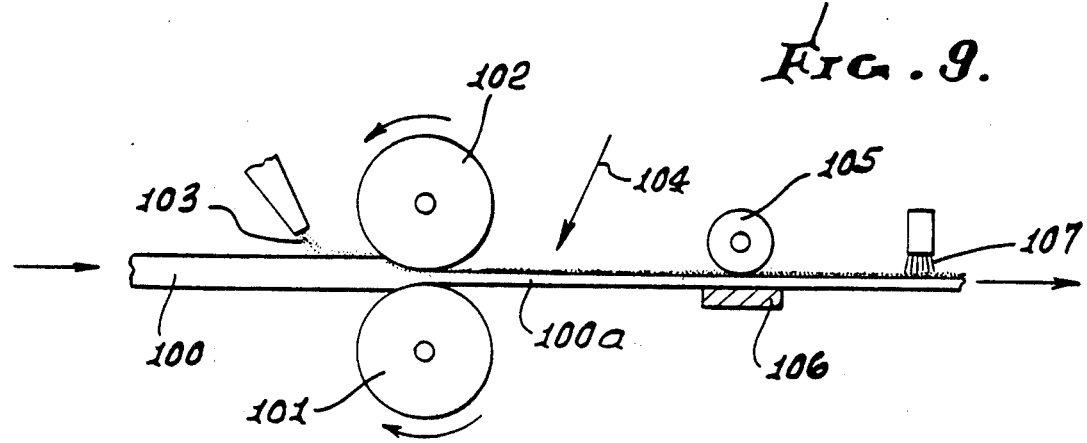
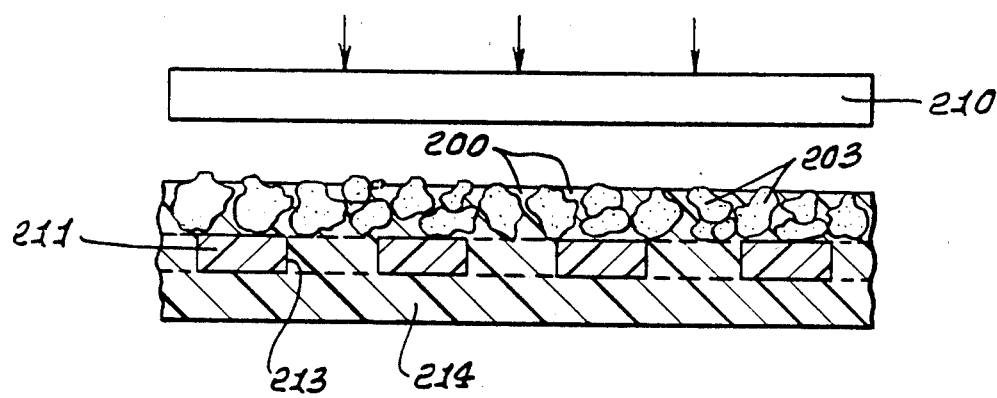
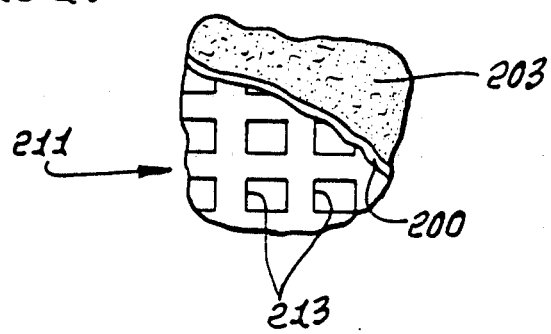

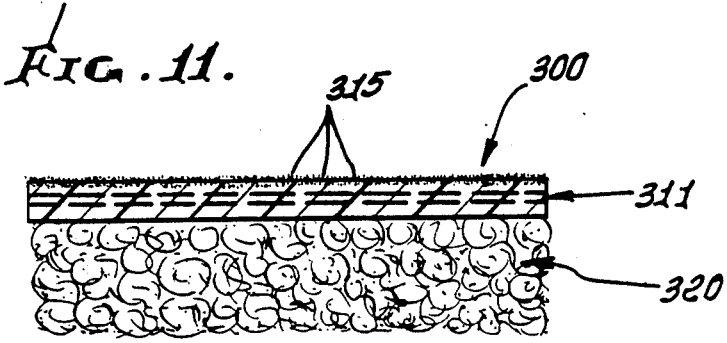
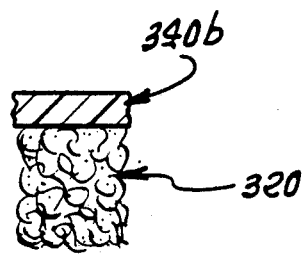
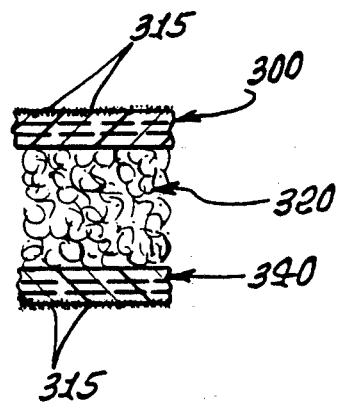
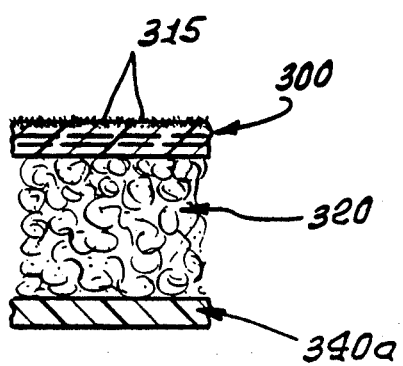

USE OF FLEXIBLE ABRASIVE PAD FOR WET ETCHING OF FINGERNAILS

BACKGROUND OF THE INVENTION

This application is a continuation-in-part of my prior application Ser. No. 356,830, filed Mar. 10, 1982 now U.S. Pat. No. 4,459,987.

This invention relates generally to cosmetic abrasive devices, and more particularly concerns a tough, flexible and stretchable abrasive sheet that may be die cut or formed to many configurations useful in abrading skin surfaces as during callous removal, dermabrasive and other skin removal techniques.

At the present time, rigid abrading stones and unstretchable devices are manipulated to effect skin removal. Such rigid or unstretchable devices do not desirably conform to complexly curved skin contours, as for example at heels, elbows, etc., and consequently they are difficult to manipulate accurately to remove skin at selected areas only. As a result, skin "burns" can and do occur, and excess time is consumed in achieving selected skin area removal. There is need for a means which will obviate these difficulties.

SUMMARY OF THE INVENTION

It is a major object of the invention to provide a stretchable, variable shape material offering a solution to the above difficulties. Basically, the stretchable cosmetic abrasive sheet of the invention comprises a tough, shaped, flexible sheet of silicone rubber and abrasive particulate, compounded so that at least one side of the sheet will have particulate exposed edges for rubbing contact with human skin during use. As will be seen, this sheet is preferably stretchable and compressible to enhance its compatibility to skin contours such as heels and elbows; further, the particulate preferably comprises pumice particles or the like. Also, the sheet thickness is between 0.015 and 0.100 inches. Further, two such sheets may be bonded together to provide a composite sheet, as will be seen.

The method of making the described sheet comprises the steps:

(a) forming a layer of incompletely cured silicone rubber, (b) combining abrasive particulate such as pumice with the rubber to adhere thereto, and (c) allowing the layer to cure to form a sheet with the particulate exposed at one side thereof for ultimate rubbing contact with human skin during use.

As will appear, the silicone-pumice initially contains a curing agent which disperses as the sheet cures. These and other objects and advantages of the invention as well as the details of an illustrative embodiment, will be more fully understood from the following description and drawings, in which:

A further aspect of the invention concerns the method of wet etching a natural or artificial fingernail, that includes (a) providing a tough, flexible sheet of silicone polymer, the sheet carrying abrasive particulate protruding from at least one side of the sheet, and (b) rubbing a side of the wet sheet against the surface of the wet fingernail.

As will appear, the etching pad is typically sufficiently thin to enable feeling of the nail, natural or artificial, through the sheet or pad during rubbing, carried out manually; and both path and nail may be pre-wetted and/or sterilized prior to such wet etching, as will appear.

DRAWING DESCRIPTION

FIG. 1 is a plan view of a die cut or formed sheet or pad embodying the invention;

FIG. 2 is an edge view taken on lines 2—2 of FIG. 1;

FIG. 3 is an enlarged fragmentary section taken on lines 3—3 of FIG. 2;

FIG. 4 is an elevation showing one step in formation of the FIG. 1 sheet or pad;

FIG. 5 is a view like FIG. 4 showing another step in formation of the sheet or pad; and FIGS. 6, 7 and 8 are views like FIG. 3 showing modified sheet or pad constructions;

FIG. 9 is a side view showing a modified method of forming the silicone layer;

FIG. 10 is an enlarged side elevation showing a method of pressing particulate into the silicone layer;

FIG. 10a shows a matte on which the silicone layer may be formed; and

FIGS. 11–14 are elevations showing modifications;

DETAILED DESCRIPTION

Figure 15:
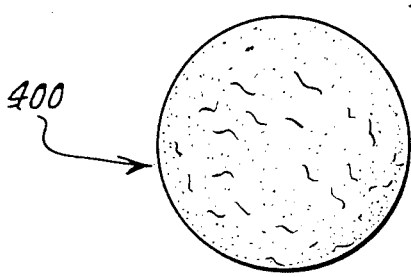
FIG. 15 is a plan view of a wet etching pad.
Figure 16:
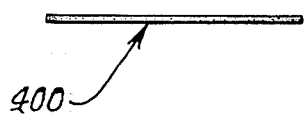
FIG. 16 is a side view of the FIG. 15 pad.

In FIGS. 1–3, a flexible, flat abrasive sheet is shown at 10, it also being somewhat stretchable to conform to contours of the body such as heels, elbows, etc. The sheet is also resiliently compressible in the direction 11, normal to the plane it defines. The sheet may preferably be die cut to shape, as for example lengthwise elongated, with rounded ends as at 10a.

The sheet preferably consists of pourable silicone polymer or adhesive sealant as for example General Electric RTV 108 which vulcanizes at room temperature. It contains a suitable curing agent. Also usable is GE RTV 118 which is self leveling when poured on a surface. RTV 108 and 118 are both translucent, tough and durable. The sheet is loaded with, or carries, abrasive particulate such as pumice or other fine abrasive suitable to abrading thickened areas of the skin. As shown, the protruding particulate 12 is located at at least one side of the sheet, and exposed for rubbing contact with the skin. FIG. 3 shows another like layer 12a at the opposite side of the sheet. The central layer 13 of silicone carries the particulate layers which are bonded to the silicone during curing, edges of particles penetrating the silicone mass. Note that particulate also covers the sheet or pad peripheral edges, as at 10b and 10a in FIG. 2, but this may be omitted.

Typically, the sheet thickness "t" is between 0.015 and 0.100 inches, and preferably between 0.020 and 0.060 inches.

In FIG. 6, the sheet or pad 100 includes a first sheet 10 having particulate 12 on one side, and a second sheet 20 having particulate 22 on one side. The two sheets have their opposite sides 13 and 23 bonded together as during curing so that the particulate layers 12 and 22 are exposed at opposite sides of the pad. In FIG. 7 the construction is the same, excepting for a separate bonding layer 33 attached to sides 13 and 23. Layer 33 may consist of polyester matte or other stretchable flexible fiber. FIG. 8 shows a modified sheet or pad 200 impregnated with particulate 201, so that edges of the particulate are exposed at the opposite sides of the sheet, 202 and 203 indicating such edges.

The method of making the pad is shown in FIGS. 4 and 5. In FIG. 4 the silicone polymer, is poured or spread at 40 on a flat surface 41. That surface advantageously consists of polyethylene at room temperature, so that the silicone will not adhere to same. Pumice particles are than dispensed as at 42 to cover the upper side 43a of the silicone layer 43 prior to complete curing. The particles become bonded to the silicone, and as the latter cures, the acetoxy or other curing agent vaporizes. The resultant sheet or pad has generally uniform thickness, and may be cut to shape. After about 15 to 20 minutes from time of pour at 40, the silicone layer or sheet is cured, at room temperature.

One usable silicone formulation is known as dimethyl polysiloxane, and the curing agent is acetic anhydride.

Another feature of the invention is to embody a finer grade of particle fineness at layer 12, and a coarser grade of particle fineness at layer 12a, as in FIG. 3.

Representative finenesses are as follows:

Fineness "A" (passes Tyler screen of mesh size 60, but will not pass screen mesh 80).

Fineness "B" (passes Tyler screen of mesh size 120, but will not pass screen mesh 140).

In FIG. 9, the sheet 100 (corresponding to sheet 10), prior to complete curing, is reduced in thickness, as by passage between calender rolls 101 and 102, thereby to form the final sheet 100a. Pumice such as particulate may be dispensed at 103 onto the upper surface of the sheet prior to passage of the sheet between the rolls, in which event the pumice is pressed into the sheet as by the roll 102. Alternatively, the pumice may be dispensed at 104 onto the sheet after it emerges from between the rolls 101 and 102. A presser unit, such as roller 105, may then be used to press the pumice into the sheet 100a as it slides over a backer 106, prior to completion of cure. A brush or compressed air stream, at 107, removes excess pumice from the sheet.

In FIGS. 10 and 10a the pumice particles 203 are shown as having been pressed, as by bar 210, into the silicone layer 200, so that the particle edges protrude from the layer 200. A matte sheet 211 in layer or sheet 200 supports the pumice, as shown. The matte contains mesh openings 213 into which the silicone layer extends, i.e. matte 211 is embedded in layer 200 and offers additional support to same. The matte may consist of polyester, NYLON, etc; it is stretchable (to stretch with layer 200); and it typically has a loose weave or configuration.

If desired, the FIG. 10 sheet can be inverted, and pumice particles pressed into area 214, in the same manner as particles 203 extend in layer 200.

In FIG. 11, the flexible first sheet is like that shown at 200 in FIG. 10, with a matte 311 embedded in the silicone polymer layer 300. Particulate (pumice for example) particles 315 are carried by the layer 300, as in FIG. 10, with edges exposed at a first side for relatively heavy duty dermabrasion (elbows, feet, etc.). A second sheet or layer 320 of reticulated foam that is resiliently compressible is attached to the sheet or layer 300, and projects at the second side thereof, as shown. The attachment may be effected by contacting one side of layer 320 with the uncured or partially cured layer 300, and allowing the cure to proceed to completion. Examples of the open work, fibrous sheet 320 are:

No. 3 Scott Industrial Foam, a reticulated polyester urethane product of Wilshire Foam Products Inc. Carson, Calif.

No. 4 Scott Safety Foam, reticulated urethane ester product of Wilshire Foam Products, Inc.

Such foam is useful for lighter dermabrasion and cleaning as well as massaging of more sensative skin areas, as face and neck. Thus, one device, as in FIG. 11, may have multiple functions, and the functional layers assist in supporting one another. Also, the openwork layer 320 is easily cleaned or freed of removed skin particles and soils, as by washing.

The device of FIG. 13 is like that of FIG. 12, and a third layer 340 is attached to the opposite side of the second layer 320. Third layer 340 is like layer 300, whereby the dermabrasion layers are interconnected by compressible layer 320. FIG. 14 is like FIG. 13, excepting that layer 340a contains no particulate. FIG. 12 is like FIG. 14, excepting that no layer 300 is used, layer 340b contains no particulate, and may consist of flexible, tough material.

Layer 320 is characterized as remaining distended after use; it does not "yellow" or discolor; and it has excellent wet abrading capability.

The thickness of layers 300, 340 and 340a are exaggerated in FIGS. 11-14.

Figure 17:
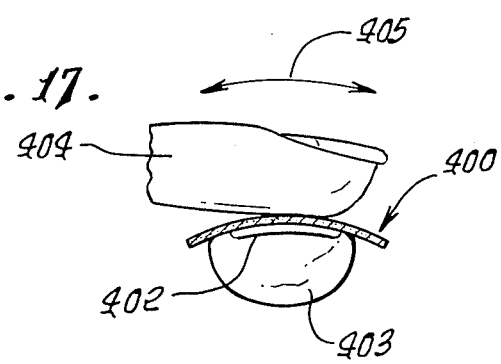
FIG. 17 is a frontal view of a finger showing the FIG. 15 pad, in use.
Figure 18:
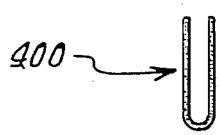
FIG. 18 is a view of the FIG. 15 pad in folded condition.

In FIG. 15, a sheet or pad 400 may have the polymer and particulate composition of the FIG. 1 sheet, or of other sheets described above. It is preferably in pad configuration, as for example generally circular, with diameter between about 1 and 2½ inches. It is used for wet etching a natural or artificial fingernail, designated at 401 in FIG. 17. The pad is stretchable and has thickness less than 3/32 inch, to enable contour feeling, therethrough, of the nail. The particulate may consist of pumice, as before. The pad may be folded as in FIG. 18 to enable the more rigid fold to be rubbed against nail cuticle, for removing same, in wet condition. Wet rubbing, etching, etc. prevents formation of objectionable dust, and the wetting agent used with the natural nail typically consists of cleaning solution (detergent or alcohol in water for example) which acts to soften cuticle, lift and remove excess oils, and sterilize the surfaces being etched. Etching enables subsequent application and attachment of conventional acrylic polymer to form the artificial nail body, and surface. See the FIG. 19 sequence of steps. The basis method includes the steps:

(a) providing a tough, flexible sheet of silicone polymer, the sheet carrying abrasive particulate protruding from at least one side of the sheet, and (b) rubbing a side of the wet sheet against the surface of the wet fingernail.

Figure 19:
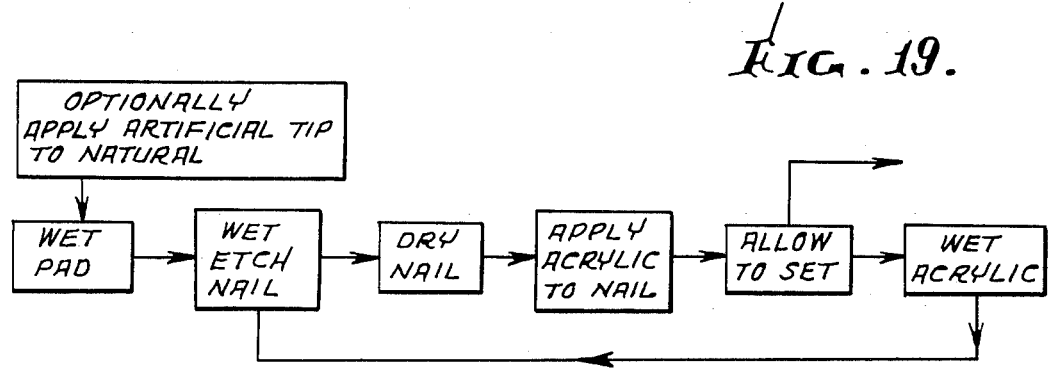
FIG. 19 is a flow diagram.

Further, the nail 402 on finger 403 may be prewetted, as in FIG. 19, by dipping into a cleaning solution prior to rubbing it with pad 400. See rubbing finger 404 in FIG. 17 pushing curved pad 400 back and forth, indicated by means 405. That solution draws excess natural oil in a fingernail to the surface, for removal by the wet etch. Subsequent drying of the nail enables good attachment of an acrylic polymer coating applied to the nail. Thereafter, that coating may be wet etched by pad 400, for example to enable fine finishing of the acrylic coating over a natural nail and/or application of a plastic tip.

In FIG. 19, an artificial nail tip may be applied onto the natural nail prior to the wet etch of the nail and tip.

I claim:

1. A flexible cosmetic abrasive sheet suitable for wet etching a natural or artificial fingernail, by rubbing contact therewith, that comprises
   (a) a tough, flexible, thin, foldable and stretchable pad of silicone polymer, and
   (b) abrasive pumice or pumice like particulate at least partially embedded in and below the outer surface of the silicone polymer pad to be directly carried thereby, and the particulate protruding from at least one side of the pad and exposed for rubbing contact with said fingernail, the particulate embedded in the polymer being cure-bonded thereto as a result of final curing of the polymer.

2. The pad of claim 1 which has thickness less than about 3/32 inch.

3. The pad of claim 2 which is generally circular, and has a diameter between about 1 and 2½ inches.

4. The sheet of claim 1 which is formed from a layer of incompletely cured silicone polymer with which the particulate is combined to adhere to the sheet, with edges of the particulate penetrating the silicone, the sheet then allowed to cure, and being stretchable with said particulate embedded therein.

* * * * *